United States Patent
Jackson et al.

[11] Patent Number: 5,925,666
[45] Date of Patent: Jul. 20, 1999

[54] PHARMACEUTICAL COMPOSITIONS AND METHODS FOR TREATING COMPULSIVE DISORDERS USING PYRROLIDINE DERIVATIVES

[75] Inventors: Paul F. Jackson, Bel Air; Barbara S. Slusher, Kingsville, both of Md.

[73] Assignee: Guilford Pharmaceuticals Inc., Baltimore, Md.

[21] Appl. No.: 08/897,564

[22] Filed: Jul. 21, 1997

Related U.S. Application Data

[63] Continuation-in-part of application No. 08/580,607, Dec. 29, 1995, Pat. No. 5,650,521.

[51] Int. Cl.$^6$ .................................................. A61K 31/40
[52] U.S. Cl. .................................................. 514/428; 514/424
[58] Field of Search ........................ 514/424, 428

[56] References Cited

U.S. PATENT DOCUMENTS

| | | | |
|---|---|---|---|
| 4,762,843 | 8/1988 | Caprathe et al. | 514/293 |
| 5,039,802 | 8/1991 | Blacklock et al. | 546/165 |
| 5,180,729 | 1/1993 | Cook | 514/317 |
| 5,262,428 | 11/1993 | Davies et al. | 514/304 |
| 5,268,480 | 12/1993 | Kozikowski | 546/23 |
| 5,298,509 | 3/1994 | Schuster et al. | 514/284 |

FOREIGN PATENT DOCUMENTS

4341605A1  8/1995  Germany.

OTHER PUBLICATIONS

"Catalytic Asymmetric Induction, Highly Enantioselective Addition of Dialkylzincs to Aldehydes Using Chiral Pyrrolidinylmethanols and Their Metal Salts," Soai et al., *J. Am. Chem. Soc.* 1987, 109, 7111–7115.

"Azacycloalkanes. III. Tertiary.alpha.–azacycloalkyl-carbinols. Synthesis and pharmacological activity," Likhosherstov et al., *Khim.–Farm. Zh.*, 1(1), pp. 27–31 1967.

"Azacycloalkanls. III. Tertiary.alpha.–azacycloalkyl-carbinoes. Synthesis and pharmacological activity," Likhosherstov et al., *Khim–Farm. Zh.*, (1967), 1(1), pp. 30–35.

*Primary Examiner*—Johann Richter
*Assistant Examiner*—Jane C. Oswecki
*Attorney, Agent, or Firm*—Gary M. Nath; Suet M. Chong; Nath & Associates

[57] ABSTRACT

The present invention relates to pharmaceutical compositions and methods for treating compulsive disorders using pyrrolidine derivatives.

18 Claims, 2 Drawing Sheets

\* p < 0.05

PHARMACEUTICAL COMPOSITIONS AND METHODS FOR TREATING COMPULSIVE DISORDERS USING PYRROLIDINE DERIVATIVES

This application is a continuation-in-part of U.S. patent application Ser. No. 08/580,607, filed on Dec. 29, 1995, now U.S. Pat. No. 5,650,521, the entire contents of which are herein incorporated by reference.

FIELD OF THE INVENTION

The present invention relates to pharmaceutical compositions and methods for treating compulsive disorders using pyrrolidine derivatives.

BACKGROUND OF THE INVENTION

Dopamine is one of the principal neurotransmitters in the central nervous system (CNS), where it is involved with motor function, perception, arousal, motivation and emotion. Abnormalities in dopaminergic neurotransmission have been implicated in various neurological and psychiatric disorders, including Parkinson's disease, depression, attention deficit disorder (ADD) and drug dependence.

The major pathway by which monoamines are inactivated is by being transported back into the cell that released them via specific transporter proteins (i.e. serotonin, norepinephrine and dopamine transporter proteins). The dopamine transporter protein (DAT) is the carrier molecule which transports dopamine across the synaptic membrane (Hitri et al., Clinical Neuropharmacology, 1994, 17, 1–22). The human dopamine transporter protein was recently cloned and shown to have several binding sites, including a binding site for cocaine (Giros et al., Mol. Pharmacol., 1992, 42, 383–390).

In the last decade, the molecular site of cocaine's addictive properties has been determined to be the DAT (Kuhar et al., TIPS, 1991, 14, 299–302). It was originally proposed that cocaine was a competitive inhibitor of dopamine uptake, coincident with cocaine and dopamine having common binding domains on the DAT. However, recent evidence suggests that dopamine and cocaine binding sites on the DAT are distinct (Kityama et al., Proc. Natl. Acad. Sci. USA, 1992, 89, 7782–7785).

Partial agonists and/or antagonists at the cocaine site on the DAT may show efficacy in treating cocaine addiction. Importantly, several compounds which bind to the cocaine binding site have been shown to block the effects of cocaine in vivo. For example, GBR 12909 has been shown to attenuate cocaine-induced activation of mesolimbic dopamine neurons in rat (Baumann et al., J. Pharm. Exp. Therap., 1994, 271, 1216–1222). Accordingly, compounds which bind to the cocaine site but do not inhibit dopamine uptake (i.e. a cocaine antagonist) may have utility in the treatment of cocaine addiction (Carroll et al., Pharmaceutical News, 1994, 1, 11–17).

Compounds which bind at the cocaine site and are not completely selective may inhibit dopamine reuptake. Studies have demonstrated that such compounds are effective or potentially effective in treating neuropsychiatric disorders characterized by abnormal dopaminergic neurotransmission, including Parkinson's disease (Mayer et al., MPTP: Neurotoxin Prod. Parkinsonian Syndr., Markey et al. (Ed.), 1985, 585–589); depression (Nielsen et al., Adv. Biosci., 1990, 77, 101–108; Randrup et al., Psychopharmacology, 1977, 52, 73–77; Halaris et al., Biochem. Pharmacol., 1975, 24, 1896–1897); attention deficit disorder (ADD) (Volkow et al., Arch. Gen. Psychiatry, 1995, 52, 456–63); and compulsive disorders (Goodman et al., International Clinical Psychopharmacology, 1992, 7(Suppl. 1), 35). Although dopamine uptake inhibitors have been proposed for treating drug dependence in general (Caine et al., Science, 1993, 260, 1814), there has been a dearth of evidence supporting their effectiveness in treating alcohol or nicotine addiction. At best, dopamine uptake inhibitors have been reported to antagonize the behavioral effects of nicotine in mice (Lerner-Marmarosh et al., Life Sci., 1995, 56, PL67–70).

Besides drug dependence, deficits in dopamine function have also been associated with pathological gambling, ADD, Tourette's syndrome, compulsive overeating and obesity. In fact, a common genetic anomaly in the dopamine $D_2$ receptor has been found among people with alcoholism, cocaine dependence, nicotine dependence, pathological gambling, attention deficit disorder (ADD), Tourette's syndrome, compulsive overeating and obesity (U.S. Pat. No. 5,621,133).

Like ethanol and other drugs of abuse, food can produce euphoria or pleasure when consumed. Although the precise localization and specificity of the reinforcing properties of these substances are under debate, there is general accord that they are manifested in the dopaminergic reward pathways of the brain (Hoebel, Amer. J. Clin. Nutrit., 1985, 42, 1133–1150). Evidence that the dopaminergic system may be implicated in obesity is suggested from studies showing the effectiveness of amphetamine-like drugs in weight loss (Scoville, Bray (Ed.), Obesity in Perspective, 1975, 441–443).

Pathological gambling also has many affinities to drug dependence. Clinicians have remarked on the similarity between the aroused euphoric state of the gambler and the "high" of the cocaine addict or substance abuser. Pathological gamblers express a distinct craving for the "feel" of gambling; they develop tolerance in that they need to take progressively greater risks and make progressively larger bets to reach a desired level of excitement; and they experience withdrawal-like symptoms (anxiety and irritability) when no "action" is available (Volberg et al., Amer. J. Psychiatry, 1988, 145, 502–505).

Attention deficit disorder (ADD) manifests itself primarily in children. The symptoms include an inability to remain focused on a particular task for an extended period of time (Funk et al., Pediatrics, 1993, 91, 816–819). A variety of drugs have been prescribed for this disease, including dextroamphetamine and methylphenidate. Methylphenidate appears to exert its effects by inhibiting the dopamine transporter, more specifically by binding to the cocaine site on the dopamine transporter (Volkow et al., Arch. Gen. Psychiatry, 1995, 52, 456–63). As a result, compounds which have a similar mode of action at this binding site may also show efficacy in this disease.

Tourette's syndrome is an autosomal dominant neuropsychiatric disorder characterized by a range of neurological and behavioral symptoms, including (i) the onset of the disorder before the age of 21 years, (ii) multiple motor and vocal tics, (iii) variance in the clinical phenomenology of the tics, and (iv) occurrence of quasi daily tics throughout a period of time exceeding a year. Motor tics generally include eye blinking, head jerking, shoulder shrugging and facial grimacing; while vocal tics include throat clearing, sniffling, yelping, tongue clicking and uttering words out of context. Recent studies have linked Tourette's syndrome with ADD. In studies of the two disorders, it was found that 50% to 80% of the people with Tourette's syndrome also had ADD. Furthermore, an increased number of relatives of individuals with Tourette's syndrome also had ADD (Knell et al, *Journal of Clinical Psychiatry*, 1993, 54, 331–337). The strong correlation between these disorders have led some researchers to propose that Tourette's syndrome is severe form of ADD (Comings et al., *Journal of Clinical Psychiatry*, 1989, S1, 275–280; Comings, *Annals of Clinical Psychiatry*, 1990, 6, 235–247).

There are currently no medications which effectively treat cocaine addiction. Accordingly, a need exists for compounds having an affinity for the cocaine site on a dopamine transporter protein (DAT), without inhibiting dopamine uptake, to aid in the treatment of cocaine addiction.

A further need exists for compounds which inhibit dopamine uptake to aid in the treatment of neurological disorders characterized by abnormal dopaminergic neurotransmission, particularly compulsive disorders such as drug dependence, eating disorders, pathological gambling and Tourette's syndrome.

The applicant has discovered new pharmaceutical compositions and new methods for treating the above described diseases, disorders and conditions using pyrrolidine derivatives.

SUMMARY OF THE INVENTION

The present invention relates to a pharmaceutical composition, which comprises:

(i) an effective amount of a compound of formula I

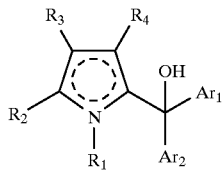

I or a pharmaceutically acceptable salt thereof, in an effective amount for treating a compulsive disorder, wherein:

the compound is an R- or S-enantiomer;

the pyrrolidine ring is saturated or unsaturated;

$R_1$, $R_2$, $R_3$ and $R_4$ are independently selected from the group consisting of hydrogen, $C_1$–$C_6$ alkyl, hydroxy, carboxy and alkoxy, wherein said $C_1$–$C_6$ alkyl is unsubstituted or substituted; and $Ar_1$ and $Ar_2$ are independently selected from the group consisting of an unsubstituted phenyl radical, a monosubstituted phenyl radical, and a multisubstituted phenyl radical, with substituents selected from the group consisting of halogen, $C_1$–$C_6$ alkyl, substituted alkyl, hydroxy, alkoxy, carboxy and mixtures thereof; and (ii) a pharmaceutically acceptable carrier, excipient, diluent or combination thereof.

The present invention further relates to a method for treating a compulsive disorder, which comprises administering to a patient suffering therefrom an effective amount of a compound of formula I

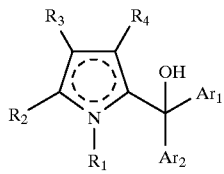

I or a pharmaceutically acceptable salt thereof, wherein:

the compound is an R- or S-enantiomer;

the pyrrolidine ring is saturated or unsaturated;

$R_1$, $R_2$, $R_3$ and $R_4$ are independently selected from the group consisting of hydrogen, $C_1$–$C_6$ alkyl, hydroxy, carboxy and alkoxy, wherein said $C_1$–$C_6$ alkyl is unsubstituted or substituted; and $Ar_1$ and $Ar_2$ are independently selected from the group consisting of an unsubstituted phenyl radical, a monosubstituted phenyl radical, and a multisubstituted phenyl radical, with substituents selected from the group consisting of halogen, $C_1$–$C_6$ alkyl, substituted alkyl, hydroxy, alkoxy, carboxy and mixtures thereof.

DETAILED DESCRIPTION OF THE INVENTION

Definitions

Figure 1:
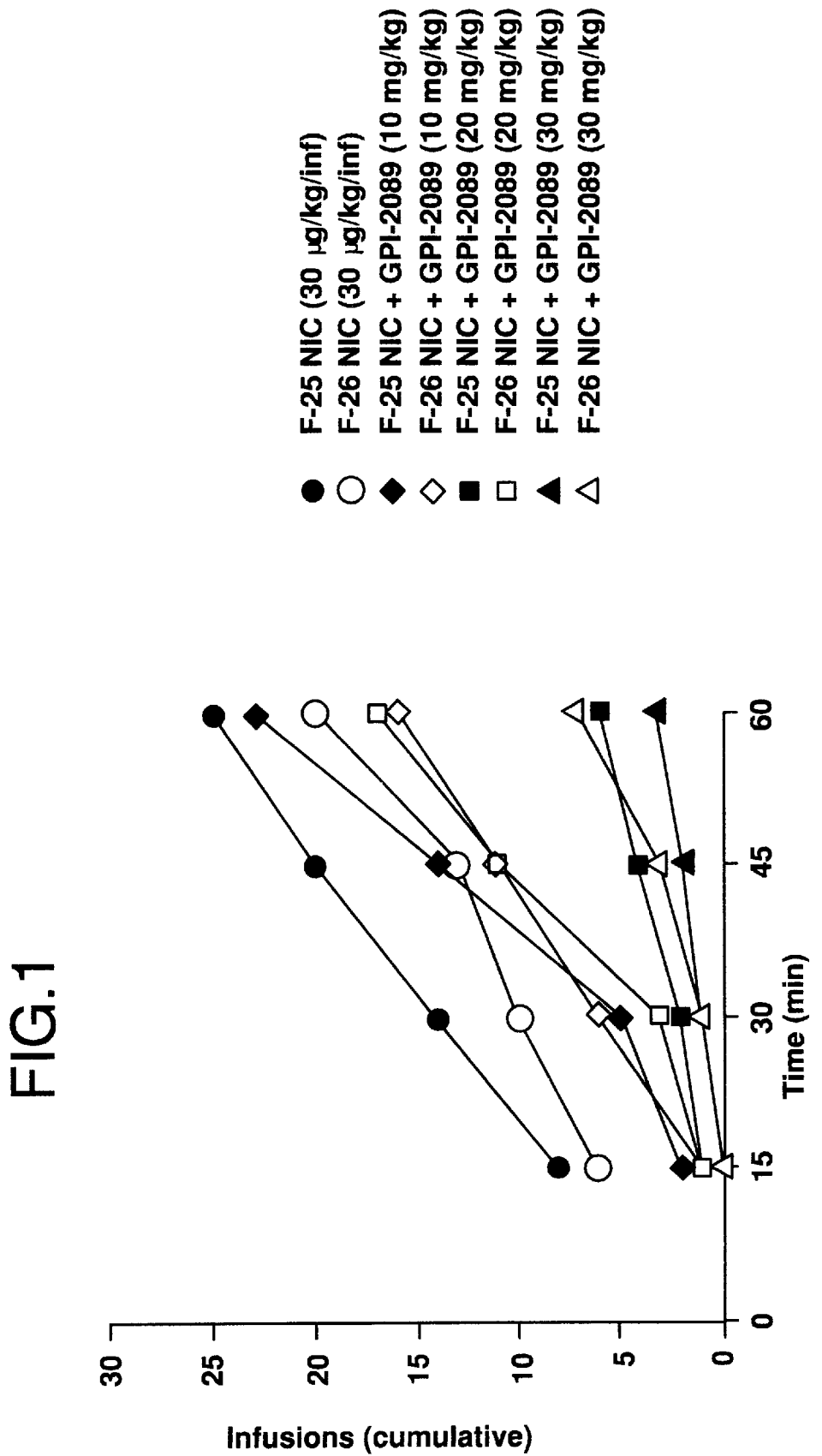
FIG. 1 is a graph plotting the cumulative nicotine infusion of rats treated with vehicle or various doses of (R)-(+)-α,α-diphenyl-2-pyrrolidine.

"Attention Deficit Disorder" refers to a disorder characterized by developmentally inappropriate inattention and impulsivity, with or without hyperactivity. Inattention means a failure to finish tasks started, easy distractibility, seeming lack of attention, and difficulty concentrating on tasks requiring sustained attention. Impulsivity means acting before thinking, difficulty taking turns, problems organizing work, and constant shifting from one activity to another. Hyperactivity means difficulty staying seated and sitting still, and running or climbing excessively. ADD is prevalent among pre-adolescent children and is reflected in poor school performance and social behavior and has been described in experimental reports of impaired perceptual, cognitive and motor function.

"Alkyl" means a branched or unbranched saturated hydrocarbon chain containing 1 to 6 carbon atoms, such as methyl, ethyl, propyl, iso-propyl, butyl, iso-butyl, tert-butyl, n-pentyl, n-hexyl, and the like, unless otherwise indicated.

"Alkoxy" means the group —OR wherein R is alkyl as herein defined. Preferably, R is a branched or unbranched saturated hydrocarbon chain containing 1 to 3 carbon atoms.

"Compulsive disorder" refers to any disorder characterized by irresistible impulsive behavior. Examples of compulsive disorders include without limitation drug dependence, eating disorders, pathological gambling, ADD and Tourette's syndrome.

"Drug dependence" refers to a psychologic addiction or a physical tolerance to a drug. Tolerance means a need to increase the dose progressively in order to produce the effect originally achieved by smaller amounts.

"Eating disorder" refers to compulsive overeating, obesity or severe obesity. Obesity means body weight of 20% over standard height-weight tables. Severe obesity means over 100% overweight.

"GPI-2089" refers to (R)-(+)-α,α-diphenyl-2-pyrrolidinemethanol.

"Halo" means fluoro, chloro, bromo or iodo, unless otherwise indicated.

"Optional" or "optionally" means that the subsequently described event or circumstance may or may not occur, and that the description includes instances where said event or circumstance occurs and instances in which it does not. For example, "optionally substituted phenyl" means that the phenyl may or may not be substituted and that the description includes both unsubstituted phenyl and substituted phenyl.

"Pathological gambling" is a condition characterized by a preoccupation with gambling. Similar to psychoactive substance abuse, its effects include development of tolerance with a need to gamble progressively larger amounts of money, withdrawal symptoms, and continued gambling despite severe negative effects on family and occupation.

"Pharmaceutically acceptable salt" refers to a salt of the inventive compounds which possesses the desired pharmacological activity and which is neither biologically nor otherwise undesirable. The salt can be formed with inorganic acids such as acetate, adipate, alginate, aspartate, benzoate, benzenesulfonate, bisulfate butyrate, citrate, camphorate, camphorsulfonate, cyclopentanepropionate, digluconate, dodecylsulfate, ethanesulfonate, fumarate, glucoheptanoate, glycerophosphate, hemisulfate heptanoate, hexanoate, hydrochloride hydrobromide, hydroiodide, 2-hydroxyethanesulfonate, lactate, maleate, methanesulfonate, 2-naphthalenesulfonate, nicotinate, oxalate, thiocyanate, tosylate and undecanoate. Examples of a base salt include ammonium salts, alkali metal salts such as sodium and potassium salts, alkaline earth metal salts such as calcium and magnesium salts, salts with organic bases such as dicyclohexylamine salts, N-methyl-D-glucamine, and salts with amino acids such as arginine and lysine. The basic nitrogen-containing groups can be quarternized with agents including lower alkyl halides such as methyl, ethyl, propyl and butyl chlorides, bromides and iodides; dialkyl sulfates such as dimethyl, diethyl, dibutyl and diamyl sulfates; long chain halides such as decyl, lauryl, myristyl and stearyl chlorides, bromides and iodides; and aralkyl halides such as benzyl and phenethyl bromides.

"Phenyl" includes all possible isomeric phenyl radicals, optionally monosubstituted or multi-substituted with substituents selected from the group consisting of alkyl, alkoxy, hydroxy, halo and haloalkyl.

"Stereoisomers" refers to isomers that differ only in the way the atoms are arranged in space. "Isomers" are different compounds that have the same molecular formula. "Enantiomers" are a pair of stereoisomers that are non-superimposable mirror images of each other. "Diastereoisomers" are stereoisomers which are not mirror images of each other. "Racemic mixture" is a mixture containing equal parts of individual enantiomers. "Non-racemic mixture" is a mixture containing unequal parts of individual enantiomers or stereoisomers.

"Therapeutically effective amount" of the dopaminergic agent means a sufficient amount of the compound to treat dopamine-related disorders at a reasonable benefit/risk ratio applicable to any medical treatment. It will be understood, however, that the total daily usage of the compounds and compositions of the present invention will be decided by the attending physician within the scope of sound medical judgement. The specific therapeutically effective dose level for any particular patient will depend upon a variety of factors including the disorder being treated; the severity of the disorder; the activity of the specific compound employed; the specific compound employed; the age, body weight, general health, sex and diet of the patient; the time of administration; the route of administration; the rate of excretion of the specific compound employed; the duration of the treatment; the drugs used in combination or coincidently with the specific compound employed; and like factors well known in the medical art.

"Tourette's syndrome" refers to an autosomal multiple tic disorder characterized by compulsive swearing, multiple muscle tics and loud noises. Tics are brief, rapid, involuntary movements that can be simple or complex; they are stereotyped and repetitive, but not rhythmic. Simple tics, such as eye blinking, often begin as nervous mannerisms. Complex tics often resemble fragments of normal behavior.

"Treating" refers to:

(i) preventing a disease, disorder or condition from occurring in an animal which may be predisposed to the disease, disorder and/or condition but has not yet been diagnosed as having it;

(ii) inhibiting the disease, disorder or condition, i.e., arresting its development; and (iii) relieving the disease, disorder or condition, i.e., causing regression of the disease, disorder and/or condition.

In relation to drug dependence, "treating" refers to suppressing the psychologic addiction or physical tolerance to the drug of abuse, and relieving or preventing a withdrawal syndrome resulting from the drug dependence.

The singular forms "a", "an" and "the" include plural references unless the context clearly dictates otherwise. Thus, for example, reference to a pyrrolidine derivative includes mixtures of such compounds and so forth.

Compounds of the Present Invention

The present invention relates to a compound of formula I

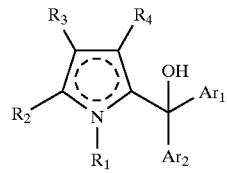

or a pharmaceutically acceptable salt thereof, wherein:
the compound is an R- or S-enantiomer;
the pyrrolidine ring is saturated or unsaturated;
$R_1$, $R_2$, $R_3$ and $R_4$ are independently selected from the group consisting of hydrogen, $C_1$–$C_6$ alkyl, hydroxy, carboxy, alkoxy and substituted $C_1$–$C_6$ alkyl group, provided that $R_1$, $R_2$, $R_3$ and $R_4$ are not all hydrogen; and
$Ar_1$ and $Ar_2$ are independently selected from the group consisting of an unsubstituted phenyl radical, a monosubstituted phenyl radical, and a multisubstituted phenyl radical, with substituents selected from the group consisting of halogen, $C_1$–$C_6$ alkyl, substituted alkyl, hydroxy, alkoxy and carboxy.

In a preferred embodiment, $R_1$ is selected from the group consisting of methyl, ethyl, propyl, butyl. In another preferred embodiment, $Ar_1$ is selected from the group consisting of 4-fluorophenyl, 4-chlorophenyl and 3-methyl-4-fluorophenyl. In a further preferred embodiment, $Ar_2$ is selected from the group consisting of 4-fluorophenyl, 4-chlorophenyl and 3-methyl-4-fluorophenyl.

In the most preferred embodiment, the compound of formula I is selected from the group consisting of:

(S)-(−)-1-methyl-α,α-diphenyl-2-pyrrolidinemethanol;
(R)-(+)-1-methyl-α,α-diphenyl-2-pyrrolidinemethanol;
(S)-(−)-1-ethyl-α,α-diphenyl-2-pyrrolidinemethanol;
(R)-(+)-1-ethyl-α,α-diphenyl-2-pyrrolidinemethanol;
(S)-(−)-1-propyl-α,α-diphenyl-2-pyrrolidinemethanol;
(R)-(+)-1-propyl-α,α-diphenyl-2-pyrrolidinemethanol;
(S)-(−)-1-butyl-α,α-diphenyl-2-pyrrolidinemethanol; and
(R)-(+)-1-butyl-α,α-diphenyl-2-pyrrolidinemethanol.

The compound of formula I possesses at least two asymmetric centers and thus can be produced as mixtures of stereoisomers (racemic and non-racemic) or as individual R- and S-stereoisomers (enantiomers and diastereoisomers). The R-stereoisomer is most preferred due to its greater activity. The individual stereoisomers may be obtained by using an optically active starting material, by resolving a racemic or non-racemic mixture of an intermediate at some appropriate stage of the synthesis, or by resolving the compounds of the present invention.

Synthesis of the Compounds of the Present Invention

Some of the compounds of formula I, such as (S)-α,α-diphenyl-2-pyrrolidinemethanol, are known and can be prepared using methods described in the art (see, for example, German Patent DE 43 41 605 A1; and U.S. Pat. No. 5,039,802).

Preferably, the compounds of formula I are prepared according to Scheme 1.

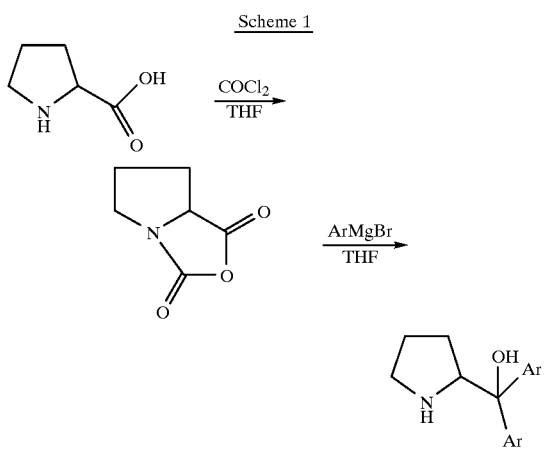

This route has been described by Mahre et al., *J. Org. Chem.*, 1991, 56, 751–762.

By using either D- or L-proline as the starting material, the final product can be obtained as either the pure R or pure S-enantiomer.

More preferably, the compounds of formula I are prepared according to Scheme 2.

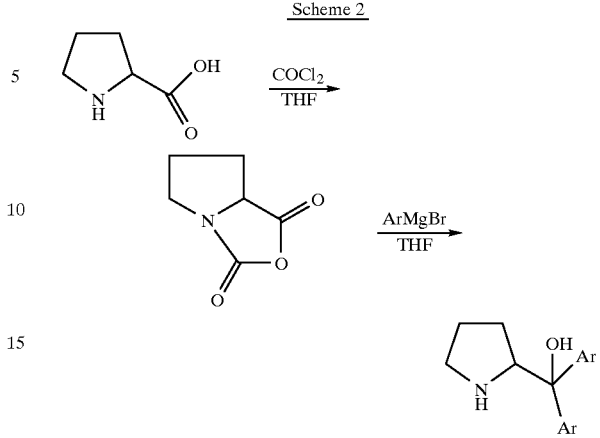

This route has been described by Kerrick et al., *J. Am. Chem. Soc.*, 1991, 113, 9708–9710.

Again, either enantiomer of the final product can be obtained by adding (+)- or (−)-sparteine to the first step.

The pyrrolidine ring and aryl groups can be substituted using methods known in the art.

Pharmaceutical Compositions of the Invention

The present invention also relates to a pharmaceutical composition, which comprises:

(i) a compound of formula I

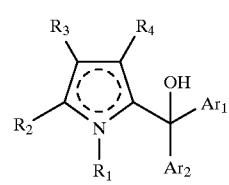

I or a pharmaceutically acceptable salt thereof, in an effective amount for treating a compulsive disorder, wherein:

the compound is an R- or S-enantiomer;
the pyrrolidine ring is saturated or unsaturated;
$R_1$, $R_2$, $R_3$ and $R_4$ are independently selected from the group consisting of hydrogen, $C_1$–$C_6$ alkyl, hydroxy, carboxy and alkoxy, wherein said substituted $C_1$–$C_6$ alkyl is substituted or unsubstituted; and
$Ar_1$ and $Ar_2$ are independently selected from the group consisting of an unsubstituted phenyl radical, a monosubstituted phenyl radical, and a multisubstituted phenyl radical, with substituents selected from the group consisting of halogen, $C_1$–$C_6$ alkyl, substituted alkyl, hydroxy, alkoxy and carboxy; and (b) a pharmaceutically acceptable carrier, excipient, diluent or combination thereof.

In a preferred embodiment, $R_1$, $R_2$, $R_3$ and $R_4$ are not all hydrogen.

In a more preferred embodiment, $R_1$ is selected from the group consisting of methyl, ethyl, propyl, butyl. In another preferred embodiment, $Ar_1$ is selected from the group consisting of 4-fluorophenyl, 4-chlorophenyl and 3-methyl-4-fluorophenyl. In a further preferred embodiment, $Ar_2$ is selected from the group consisting of 4-fluorophenyl, 4-chlorophenyl and 3-methyl-4-fluorophenyl.

In the most preferred embodiment, the compound is selected from the group consisting of:

(S)-(−)-1-methyl-α,α-diphenyl-2-pyrrolidinemethanol;
(R)-(+)-1-methyl-α,α-diphenyl-2-pyrrolidinemethanol;
(S)-(−)-1-ethyl-α,α-diphenyl-2-pyrrolidinemethanol;
(R)-(+)-1-ethyl-α,α-diphenyl-2-pyrrolidinemethanol;
(S)-(−)-1-propyl-α,α-diphenyl-2-pyrrolidinemethanol;
(R)-(+)-1-propyl-α,α-diphenyl-2-pyrrolidinemethanol;
(S)-(−)-1-butyl-α,α-diphenyl-2-pyrrolidinemethanol; and
(R)-(+)-1-butyl-α,α-diphenyl-2-pyrrolidinemethanol.

The compulsive disorder may be any disorder characterized by irresistible impulsive behavior. Examples of compulsive disorders treatable by the methods of the present invention include without limitation drug dependence, eating disorders, pathological gambling, ADD and Tourette's syndrome. Preferably, the compulsive disorder is drug dependence. More preferably, the drug dependence is alcohol or nicotine dependence.

In another preferred embodiment, the compound or the pharmaceutically acceptable salt thereof has an affinity for the cocaine binding site on a dopamine transporter protein (DAT).

In a more preferred embodiment, the compound or the pharmaceutically acceptable salt thereof permits a dopamine transporter protein (DAT) to maintain its function of accumulating dopamine.

In the most preferred embodiment, the compound or the pharmaceutically acceptable salt thereof antagonizes cocaine's binding to a dopamine transporter protein (DAT) while permitting the DAT to maintain its function of accumulating dopamine.

In a further preferred embodiment, the compound or the pharmaceutically acceptable salt thereof has an uptake to binding ratio ($Ki_{uptake}/Ki_{binding}$) greater than that of cocaine.

In a more preferred embodiment, the compound or the pharmaceutically acceptable salt thereof has an uptake to binding ratio ($Ki_{uptake}/Ki_{binding}$) of at least 2.

Route of Administration

The compounds or pharmaceutical compositions of the present invention may be administered orally, parenterally, by inhalation spray, topically, rectally, nasally, buccally, vaginally or via an implanted reservoir in dosage formulations containing conventional non-toxic pharmaceutically-acceptable carriers, adjuvants and vehicles. The term parenteral as used herein includes subcutaneous, intravenous, intramuscular, intraperitoneal, intrathecal, intraventricular, intrasternal or intracranial injection and infusion techniques. Invasive techniques are preferred, particularly direct administration to damaged neuronal tissue.

To be effective therapeutically as central nervous system targets, the compounds or pharmaceutical compositions should readily penetrate the blood-brain barrier when peripherally administered. Compounds or pharmaceutical compositions which cannot penetrate the blood-brain barrier can be effectively administered by an intraventricular route.

The compounds or pharmaceutical compositions may also be administered in the form of sterile injectable preparations, for example, as sterile injectable aqueous or oleaginous suspensions. These suspensions can be formulated according to techniques known in the art using suitable dispersing or wetting agents and suspending agents. The sterile injectable preparations may also be sterile injectable solutions or suspensions in non-toxic parenterally-acceptable diluents or solvents, for example, as solutions in 1,3-butanediol. Among the acceptable vehicles and solvents that may be employed are water, Ringer's solution and isotonic sodium chloride solution. In addition, sterile fixed oils are conventionally employed as solvents or suspending mediums. For this purpose, any bland fixed oil such as a synthetic mono- or di-glyceride may be employed. Fatty acids such as oleic acid and its glyceride derivatives, including olive oil and castor oil, especially in their polyoxyethylated forms, are useful in the preparation of injectables. These oil solutions or suspensions may also contain long-chain alcohol diluents or dispersants.

Additionally, the compounds or pharmaceutical compositions may be administered orally in the form of capsules, tablets, aqueous suspensions or solutions. Tablets may contain carriers such as lactose and corn starch, and/or lubricating agents such as magnesium stearate. Capsules may contain diluents including lactose and dried corn starch. Aqueous suspensions may contain emulsifying and suspending agents combined with the active ingredient. The oral dosage forms may further contain sweetening and/or flavoring and/or coloring agents.

The compounds or pharmaceutical compositions may further be administered rectally in the form of suppositories. These compositions can be prepared by mixing the drug with suitable non-irritating excipients which are solid at room temperature, but liquid at rectal temperature such that they will melt in the rectum to release the drug. Such excipients include cocoa butter, beeswax and polyethylene glycols.

Moreover, the compounds or pharmaceutical compositions may be administered topically, especially when the conditions addressed for treatment involve areas or organs readily accessible by topical application, including neurological disorders of the eye, the skin or the lower intestinal tract.

For topical application to the eye, or ophthalmic use, the compounds or pharmaceutical compositions can be formulated as micronized suspensions in isotonic, pH adjusted sterile saline or, preferably, as a solution in isotonic, pH adjusted sterile saline, either with or without a preservative such as benzylalkonium chloride. Alternatively, the compounds or pharmaceutical compositions may be formulated into ointments, such as petrolatum.

For topical application to the skin, the compounds or pharmaceutical compositions can be formulated into suitable ointments containing the active compound suspended or dissolved in, for example, a mixture of one or more of the following: mineral oil, liquid petrolatum, white petrolatum, propylene glycol, polyoxyethylene polyoxypropylene compound, emulsifying wax and water. Alternatively, the compounds or pharmaceutical compositions can be formulated into suitable lotions or creams containing the active compound suspended or dissolved in, for example, a mixture of one or more of the following: mineral oil, sorbitan monostearate, polysorbate 60, cetyl ester wax, cetearyl alcohol, 2-octyldodecanol, benzyl alcohol and water.

Topical application to the lower intestinal tract can be effected in rectal suppository formulations (see above) or in suitable enema formulations.

The compounds or pharmaceutical compositions may be administered by a single dose, multiple discrete doses or continuous infusion.

Additionally, the compounds or pharmaceutical compositions may be administered alone or in combination or in concurrent therapy with other agents, for example, dopaminergic agents, such as L-dopa, amantadine, apomorphine and bromocryptine.

If desired, the compounds or pharmaceutical compositions can be incorporated into slow release or targeted delivery systems such as polymer matrices, liposomes and microspheres. They may be sterilized, for example, by filtration through a bacteria-retaining filter, or by incorporating sterilizing agents in the form of sterile solid compositions which can dissolve in sterile water, or some other sterile injectable medium immediately before use.

The active compounds can also be in micro-encapsulated form with one or more excipients as noted above. The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferably, in a certain part of the intestinal tract, optionally in a delayed manner. Examples of embedding compositions which can be used include polymeric substances and waxes.

Dosage

Dose levels on the order of about 0.1 mg to about 10,000 mg of the active ingredient compound are useful in the treatment of the above conditions, with preferred levels being about 0.1 mg to about 1,000 mg. The specific dose level for any particular patient will vary depending upon a variety of factors, including the activity of the specific compound employed; the age, body weight, general health, sex and diet of the patient; the time of administration; the rate of excretion; drug combination; the severity of the particular disease being treated; and the form of administration. Typically, in vitro dosage-effect results provide useful guidance on the proper doses for patient administration. Studies in animal models are also helpful. The considerations for determining the proper dose levels are well known in the art.

Methods of the Present Invention

Methods for Treating Cocaine Addiction and Overdose

Cocaine exerts its reinforcing properties by facilitating the action of the neurotransmitter dopamine in the mesolimbocortical pathways of the brain, a region responsible for the regulation of pleasure and reward. Cocaine does so by inhibiting the functioning of the dopamine transporter (DAT) protein. This inhibition results in excess levels of synaptic dopamine and enhanced dopaminergic transmission.

In 1992, two independent laboratories reported the molecular cloning of the human DAT. Subsequent site-directed mutagenesis studies employing the DAT clone demonstrated that dopamine uptake and cocaine binding occur at distinct sites on the transporter protein. This is significant because it means that drugs can be designed to specifically inhibit cocaine recognition by the DAT while permitting the transporter to maintain its function of accumulating dopamine. This selectivity is important because such a drug would block the physiological effects of cocaine while leaving normal dopamine transmission within the brain intact.

Accordingly, selective cocaine antagonists and mixed agonist/antagonists may have clinical utility in the treatment of cocaine addiction and overdose. Specifically, such compounds would exhibit high uptake to binding ratios ($Ki_{uptake}/Ki_{binding}$), which mean that the compounds would bind potently to the cocaine site on the dopamine transporter protein (expressed as $Ki_{binding}$) and have little or no effect on dopamine uptake (expressed as $Ki_{uptake}$) Stated in other terms, the compounds would antagonize cocaine's binding to the DAT while exhibiting minimal effects on transport function.

Thus, the present invention also relates to a method of treating cocaine addiction or overdose, which comprises administering to a patient suffering therefrom a therapeutically effective amount of a compound of formula I

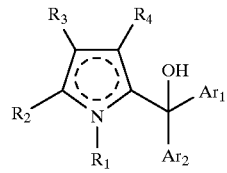

I or a pharmaceutically acceptable salt thereof, wherein:
the compound is an R- or S-enantiomer;
the pyrrolidine ring is saturated or unsaturated;
$R_1$, $R_2$, $R_3$ and $R_4$ are independently selected from the group consisting of H, $C_1$–$C_6$ alkyl, hydroxy, carboxy and alkoxy, wherein said $C_1$–$C_6$ alkyl is unsubstituted or substituted; and
$Ar_1$ and $Ar_2$ are independently selected from the group consisting of an unsubstituted phenyl radical, a monosubstituted phenyl radical, and a multisubstituted phenyl radical, with substituents selected from the group consisting of halogen, $C_1$–$C_6$ alkyl, substituted alkyl, hydroxy, alkoxy, carboxy and mixtures thereof.

Preferred compounds useful for this method are identified above in relation to pharmaceutical compositions of the present invention.

Methods for Treating Compulsive Disorders

Compounds which bind at the cocaine site and are not completely selective may inhibit dopamine reuptake. Such compounds could be useful in treating disorders characterized by abnormal dopaminergic neurotransmission, particularly compulsive disorders.

Accordingly, the present invention further relates to a method for treating a compulsive disorder, which comprises administering to a patient suffering therefrom a therapeutically effective amount of a compound of formula I

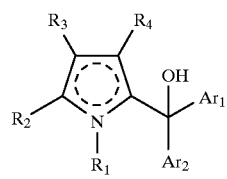

I or a pharmaceutically acceptable salt thereof, wherein:
the compound is an R- or S-enantiomer;
the pyrrolidine ring is saturated or unsaturated;
$R_1$, $R_2$, $R_3$ and $R_4$ are independently selected from the group consisting of H, $C_1$–$C_6$ alkyl, hydroxy, carboxy, alkoxy, wherein said $C_1$–$C_6$ unsubstituted or substituted; and
$Ar_1$ and $Ar_2$ are independently selected from the group consisting of an unsubstituted phenyl radical, a monosubstituted phenyl radical, and a multisubstituted phenyl radical, with substituents selected from the group consisting of halogen, $C_1$–$C_6$ alkyl, substituted alkyl, hydroxy, alkoxy, carboxy and mixtures thereof.

The compulsive disorder may be any disorder characterized by irresistible impulsive behavior. Examples of compulsive disorders treatable by the methods of the present invention include without limitation drug dependence, eating disorders, pathological gambling, ADD and Tourette's syndrome.

Preferably, the compulsive disorder is drug dependence. Commonly used drugs with potential for dependence include CNS depressants (opioids, synthetic narcotics, barbiturates, glutethimide, methyprylon, ethchlorvynol, methaqualone, alcohol); anxiolytics (diazepam, chlordiazepoxide, alprazolam, oxazepam, temazepam); stimulants (amphetamine, methamphetamine, cocaine); and hallucinogens (LSD, mescaline, peyote, marijuana).

More preferably, the drug dependence is alcohol or nicotine dependence.

Preferred compounds useful for this method are identified above in relation to pharmaceutical compositions of the present invention.

In Vitro Selectivity and Binding Potency to Cocaine Binding Site

Four compounds of formula I were tested in vitro for their ability to displace the cocaine analogue $(-)$-2-$\beta$-$[^3H]$ carbomethoxy-3$\beta$-(4-fluorophenyl)tropane binding at the cocaine site on the dopamine transporter protein (DAT) (expressed as $Ki_{binding}$), and for their ability to block dopamine uptake into neurons by inhibiting the neuronal dopamine transporter (expressed as $Ki_{uptake}$).

The following TABLE I compares the $Ki_{binding}$ and $Ki_{uptake}$ values and the uptake to binding ratios ($Ki_{uptake}$/$Ki_{binding}$) of the tested compounds with those of cocaine.

TABLE I

In Vitro Activity of Compounds of Formula I

| Compound | Affinity to the Cocaine Binding Site ($Ki_{binding}$) | Effect on Dopamine Uptake ($Ki_{uptake}$) | Uptake to Binding Ratio ($Ki_{uptake}$/$Ki_{binding}$) |
|---|---|---|---|
| Cocaine | 0.12 μM | 0.20 μM | 1.67 |
| (R)-(+)-α,α-diphenyl-2-pyrrolidinemethanol | 0.04 | 0.17 | 4.25 |
| (S)-(−)-α,α-diphenyl-2-pyrrolidinemethanol | 0.40 | 1.65 | 4.12 |
| (S)-(−)-1-propyl-α,α-diphenyl-2-pyrrolidine-methanol | 3.30 | 10.3 | 3.12 |

TABLE I-continued

In Vitro Activity of Compounds of Formula I

| Compound | Affinity to the Cocaine Binding Site ($Ki_{binding}$) | Effect on Dopamine Uptake ($Ki_{uptake}$) | Uptake to Binding Ratio ($Ki_{uptake}/Ki_{binding}$) |
|---|---|---|---|
| 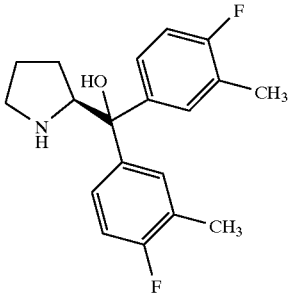<br>(s)-α,α-Bis(3-methyl-4-fluorophenyl)-2-pyrrolidine-methanol | 0.26 | 0.44 | 1.69 |

$Ki_{binding}$ represents the ability of the test compounds to inhibit the binding of the cocaine analog, CFT (a cocaine analog was used in place of cocaine in the test procedures because cocaine itself is unstable) to the DAT. Thus, the lower the $Ki_{binding}$ means the greater the ability of the test compounds to antagonize cocaine's binding to the DAT.

$Ki_{uptake}$ represents the potency of the test compounds to inhibit dopamine uptake. The higher the $Ki_{uptake}$ values means the higher the selectivity of the test compounds in binding to the cocaine site on the DAT and, thus, the lower the inhibition of the functioning of the DAT.

Based on the data in TABLE I, cocaine is non-selective with an uptake to binding ratio of 1.7. All the tested compounds of formula I exhibit uptake to binding ratios greater than that of cocaine, which mean that the compounds bind potently to the cocaine site on the DAT and have little or no effect on dopamine uptake.

Test Procedures

Values (Ki values) for the binding of compounds at the cocaine binding site of the human dopamine transporter as well as values for the inhibition of dopamine uptake can be obtained using methods described in the literature (Kitayama et al., Proc. Natl. Acad. Sci. USA, 1992, 89, 7782–7785). Below are the experimental procedures for the assay of compounds.

All assays were performed using Chinese Hamster Ovary cells stably expressing the human dopamine transporter cDNA (hDAT cells). hDAT cells were distributed in 96-well plates and grown 3 to 4 days to confluency (~$10^5$ cells/well) in Ham's F12 medium containing 10% fetal calf serum. To facilitate comparisons, dopamine uptake and cocaine analogue binding were performed under identical conditions including assay buffers, temperature and time as detailed below.

[$^3$H]Dopamine Uptake

To assess [$^3$H]dopamine uptake, the hDAT cells were washed two times in Krebs-Ringer-HEPES buffer containing 100 μM ascorbic acid (KRH+) at room temperature. Cells were then incubated with 100 nM [$^3$H]dopamine (24.1 Ci/mmol; NEN) in KRH+ buffer for 6 minutes at room temperature. Co-incubation with 100 mM unlabeled (−) cocaine in parallel incubations allowed estimation of non-specific uptake. Uptake was terminated by five washes with ice-cold KRH+ and radioactivity was quantitated using a Packard TopLoad Scintillation Counter.

For uptake inhibition studies, cells were pre-incubated with the test compound for 2 hours in cell culture medium at 37° C. Subsequently, the hDAT cells were washed two times in KRH+ buffer at room temperature. The cells were then incubated with 100 nM [$^3$H]dopamine and test compound in KRH+ buffer at room temperature for 6 minutes. Binding was terminated and quantified as above. Data was analyzed and inhibition constants (Ki) were calculated using the Origin™ computer program by Microcal Software, Inc.

[$^3$H]CFT Binding

To assess binding of the cocaine analogue (−)-2β-[$^3$H] carbomethoxy-3β-(4-fluorophenyl)tropane (CFT), the hDAT cells were washed two times in Krebs-Ringer-HEPES (KRH) buffer at room temperature. Cells were then incubated with 5 nM [$^3$H]CFT (87 Ci/mmol; NEN) in KRH buffer for 6 minutes at room temperature. Co-incubation with 100 μM unlabeled (−)cocaine in parallel incubations allowed estimation of nonspecific binding. Binding was terminated by five washes with ice-cold KRH and radioactivity was quantitated using a Packard TopLoad Scintillation Counter.

For binding inhibition studies, the hDAT cells were pre-incubated with test compound for 2 hours in cell culture medium at 37° C. Subsequently, the cells were washed three times in KRH buffer at room temperature. The cells were then incubated with 5 nM [$^3$H]CFT and test compound in KRH buffer at room temperature for 6 minutes. Binding was terminated and quantified as above. Data was analyzed and inhibition constants ($K_i$) were calculated using the Origin™ computer program by Microcal Software, Inc.

Inhibition of Ethanol Intake in Alcohol-Preferring Rats

The effect of systemic administration of (R)-(+)-α,α-diphenyl-2-pyrrolidinemethanol on ethanol intake in the alcohol-preferring (P) line of rats was performed as previously described by Panocka et al., *Pharm. Biochem. and Behavior*, 1995, 52, 2, 255–259, and Murphy et al., *Alcohol*, 1985, 2, 349–352. In brief, (R)-(+)-α,α-diphenyl-2-pyrrolidinemethanol (30 mg/kg i.p.) was tested in female P rats (n=8) given daily 1 hour scheduled access to a 10% (v/v) ethanol solution. A within-subject design was used where (R)-(+)-α,α-diphenyl-2-pyrrolidinemethanol treatments were tested once per week. Baseline ethanol drinking consisted of the mean of the 3 days prior to testing in which saline injections were given. (R)-(+)-α,α-diphenyl-2-pyrrolidinemethanol or saline, administered i.p. in 1 ml/kg volumes, were injected 10–15 minutes prior to ethanol access. Twenty-four hour water and daily body weights were recorded to assess non-specific drug effects. Results were analyzed using paired t-tests with baseline and test day values serving as the independent variables. Ethanol intake was recorded as amount of solution consumed (mls).

Figure 2A:
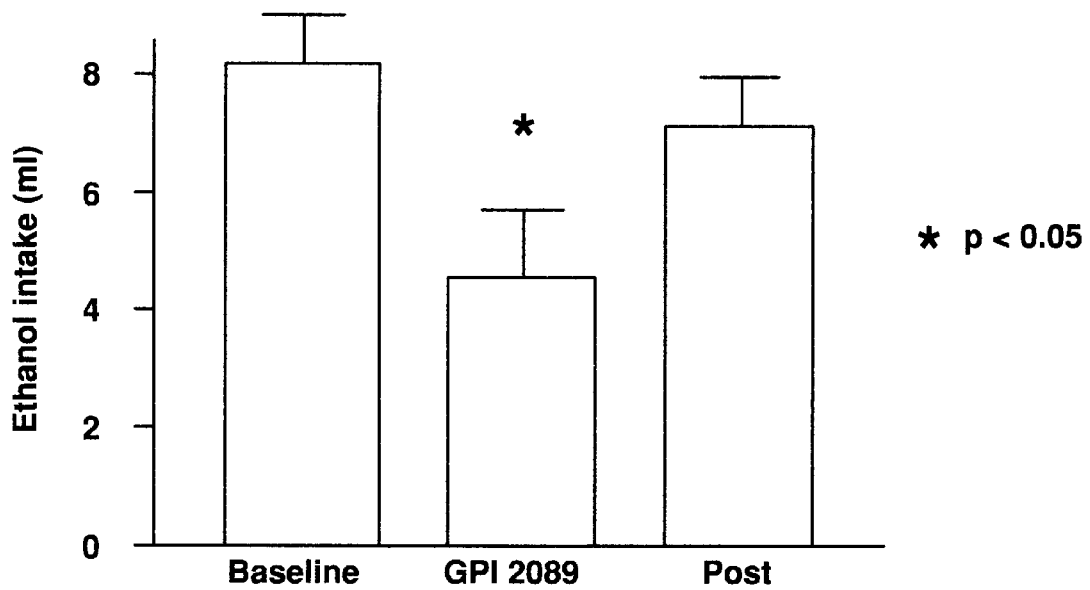
FIG. 2(a) is a bar graph plotting the ethanol intake of alcohol-preferring rats before (i.e. Baseline) and 1 hour (i.e. GPI 2089) and 24 hours after (i.e. Post) (R)-(+)-α,α-diphenyl-2-pyrrolidine treatment.
Figure 2B:
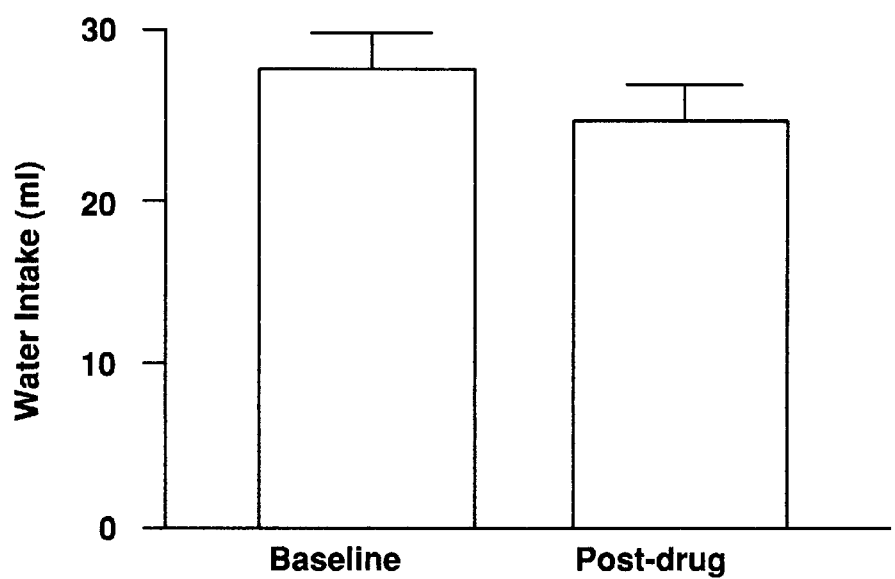
FIG. 2(b) is a bar graph plotting the water intake of the alcohol-preferring rats before (i.e. Baseline) and 24 hours after (i.e. Post) (R)-(+)-α,α-diphenyl-2-pyrrolidine treatment.

As shown in TABLE II, TABLE III and FIG. 2(*a*), (R)-(+)-α,α-diphenyl-2-pyrrolidinemethanol administered systemically at a dose of 30 mg/kg i.p. significantly reduced ethanol consumption by approximately 45% ($p<0.05$) during the 1 hour access period. Body weights of the rats were not altered. As depicted in FIG. 2(*b*), (R)-(+)-α,α-diphenyl-2-pyrrolidinemethanol had no effect on water consumption for 24 hours following administration.

1 HOUR ETHANOL CONSUMPTION

Saline Baseline: 8.2±0.8 mls 30 mg/kg (R)-(+)-α,α-diphenyl-2-pyrrolidinemethanol:
4.5±1.2 mls * ($p<0.05$)

24 HOUR WATER INTAKE

Saline Baseline: 28±2.2 mls 30 mg/kg (R)-(+)-α,α-diphenyl-2-pyrrolidinemethanol:
25±2.1 mls

24 HOUR BODY WEIGHTS

Saline Baseline: 310±6.1 g 30 mg/kg (R)-(+)-α,α-diphenyl-2-pyrrolidinemethanol:
300±6.2 g

TABLE II

Inhibition of Alcohol Intake in Alcohol-Preferring Rats

| Rat ID | Baseline Ethanol 1 hr (ml) | Baseline Ethanol 1 hr (g/kg) | Baseline Water 24 hr (ml) | Baseline Weight (g) |
|---|---|---|---|---|
| P31 | 11 | 2.7 | 24 | 332 |
| P32 | 7 | 1.8 | 21 | 290 |
| P33 | 5 | 1.4 | 42 | 294 |
| P34 | 8 | 2.1 | 30 | 313 |
| P35 | 10 | 2.3 | 35 | 334 |
| P36 | 8 | 2.1 | 25 | 307 |
| P37 | 7 | 1.9 | 22 | 298 |
| P38 | 8 | 2.0 | 27 | 319 |
| P39 | 5 | 1.4 | 23 | 282 |
| P40 | 13 | 3.3 | 29 | 327 |
| Means | 8.2 | 2.1 | 28 | 310 |
| S.E.M. | 0.8 | 0.2 | 2.2 | 6.1 |

TABLE III

Dose: 30 mg/kg (i.p.)
Inhibition of Alcohol Intake in Alcohol-Preferring Rats
Following Administration of Compounds of Formula I

| Rat ID | Test Day Ethanol 1 hr (ml) | Test Day Ethanol 1 hr (g/kg) | Post-drug Water 24 hr (ml) | Post-drug Weight (g) |
|---|---|---|---|---|
| P31 | 8 | 1.9 | 23 | 329 |
| P32 | 7 | 1.9 | spill | 291 |
| P33 | 1 | 0.3 | 26 | 294 |
| P34 | 2 | 0.5 | 28 | 305 |
| P35 | 10 | 2.4 | 26 | 290 |
| P36 | 1 | 0.3 | 32 | 297 |
| P37 | 9 | 2.4 | 18 | 297 |
| P38 | 4 | 1.0 | 32 | 312 |
| P39 | 3 | 0.8 | 12 | 263 |
| P40 | 0 | 0 | 26 | 323 |
| Means | 4.5 | 1.2 | 25 | 300 |
| S.E.M. | 1.2 | 0.3 | 2.1 | 6.2 |

Inhibition of Nicotine Self-Administration in Male Long-Evans Rats

Male Long-Evans rats were trained to self-administer nicotine on a fixed ratio schedule of reinforcement, as described by Corrigall et al., *Psychopharmacology*, Vol. 104, No. 2, pp. 171–176 (1991) and Corrigall et al., *Psychopharmacology*, Vol. 107, Nos. 2–3, pp. 285–289 (1992). In brief, male Long-Evans rats were food deprived for a short period of time (24–48 hours) and trained to press a lever in an operant responding chamber on an FR-1 schedule of food reinforcement. Once trained, each rat was surgically prepared with a chronic intravenous catheter implanted into the jugular vein. The rats were allowed 1 week to recover from surgery.

After 1 week, nicotine self-administration studies were initiated on an FR-1 with a 60 second signaled time-out following each infusion. During time-out, responding on the lever had no scheduled consequence. Nicotine self-administration sessions were 60 minutes in duration. Each nicotine infusion contained 30 μg of nicotine/kg rat and were delivered in a volume of 54 μl over an infusion duration of 0.3 seconds. 15 minutes before the self-administration sessions, the rats were pre-treated intraperitoneally with (R)-(+)-α,α-diphenyl-2-pyrrolidinemethanol at doses of 10, 20 and 30 mg/kg.

As shown in FIG. 1, (R)-(+)-α,α-diphenyl-2-pyrrolidinemethanol dose-dependently attenuated nicotine (30 μg/kg/infusion) self-administration.

EXAMPLES

The following examples are illustrative of the present invention and are not intended to be limitations thereon. All percentages are based on 100% by weight of the final compound.

Example 1

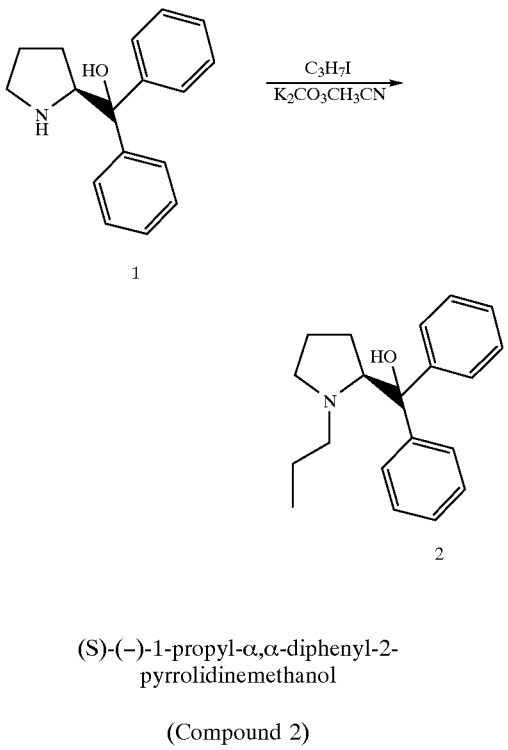

(S)-(−)-1-propyl-α,α-diphenyl-2-pyrrolidinemethanol (Compound 2)

(S)-(−)-α,α-diphenyl-2-pyrrolidinemethanol (1) (1.0 g, 4.0 mmol) was added to a flask containing potassium carbonate (1.2 g, 8.7 mmol) and 20 ml of acetonitrile. Propyl iodide (2.0 ml, 21 mmol) was added and the resulting mixture heated to reflux for three hours. At the end of this time, the mixture was cooled to room temperature, added to brine (50 ml), and extracted with ethyl acetate. The ethyl acetate layer was washed once with brine, dried over anhydrous magnesium sulfate, and the solvent removed under reduced pressure. This afforded the desired material (2) (0.98 g, 84%) as a white solid.

$^1$H NMR (DMSO-d6): 0.5 (t, 3H), 1.0–1.2 (m, 2H), 1.3–1.9 (m, 5H), 2.0–2.1 (m, 1H), 2.3 (q, 1H), 3.1 (m, 1H), 3.9 (m, 1H), 5.1 (br s, 1H), 7.0–7.3 (m, 6H), 7.5–7.7 (m, 4H).

Example 2

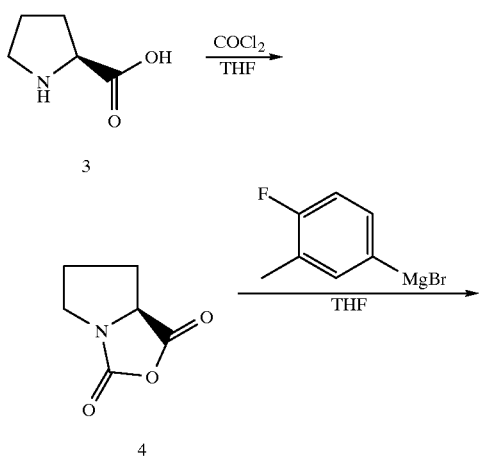

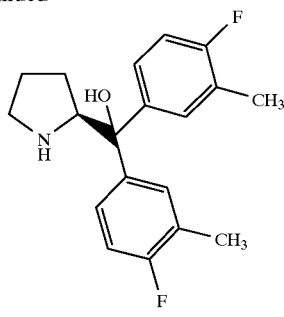

(S)-α,α-Bis(3-methyl-4-fluorophenyl)-2-pyrrolidinemethanol (Compound 5)

4-Fluoro-3-methylphenylmagnesium bromide (16.0 ml, 1.0 M in tetrahydrofuran, 32 mmol) was added to a 500 ml three neck round bottom flask containing a low temperature thermometer and a 50 ml dropping funnel. This was then cooled to −15° C. under an atmosphere of nitrogen. (S)-Tetrahydro-1H,3H-pyrrolo[1,2-c]oxazole-1,3-dione (4) (1.50 g, 10.6 mmol) in dry tetrahydrofuran (10 ml) was added to the dropping funnel. This solution was then added dropwise to the Grignard reagent at such a rate as to maintain the reaction temperature between −15° C. and −10° C. The addition was complete in approximately 45 minutes. The mixture was stirred for 2 hours at −15° C. and 1 hour at 0° C. before being poured into a precooled (0° C.) solution of sulfuric acid (25 ml, 2.0 M). After 5 minutes a thick white precipitate formed. The mixture was cooled for an additional 1 hour, filtered, and washed twice with THF (150 ml). The resulting solution was then concentrated to a volume of 50 ml. This was then cooled to 0° C. and a yellow precipitate formed. After 30 minutes, the precipitate was filtered, washed twice with 20 ml of water and twice with 50 ml of ethyl acetate. The desired material as its sulfate salt was obtained as a white solid (2.0 g, 52%). A portion of the salt (0.50 g, 0.70 mmol) was added to a 1.0 M potassium hydroxide solution (10 ml) and stirred at room temperature for 1 hour. At the end of this time, toluene (25 ml) was added and the mixture filtered. The aqueous layer was removed and the organic phase was washed once with water (25 ml). This was then dried with anhydrous magnesium sulfate and evaporated under reduced pressure to give the desired product (5) (0.37 g, 84%) as a clear and colorless oil.

$^1$H NMR (DMSO d$_6$): δ 1.6–2.2 (m, 4H), 2.1 (s, 6H), 2.3 (s, 1H), 2.8 (m, 2H), 4.15 (t, 1H), 5.1 (s, 1H), 6.9–7.0 (appt, 2H), 7.1–7.5 (m, 4H).

Example 3

(S)-Tetrahydro-1H,3H-pyrrolo[1,2-c]oxazole-1,3-dione (Compound 4)

L-Proline (11.5 g, 0.10 mol) was added to a 500 ml three neck flask fitted with a 125 ml addition funnel, thermometer and a nitrogen inlet tube. To the flask was added dry tetrahydrofuran (115 ml) and the mixture cooled to 15° C. using an ice/water bath. The addition funnel was charged with diphosgene (7.2 ml, 0.06 mol) and dry THF (50 ml).

The diphosgene solution was added dropwise to the proline mixture over 45 minutes while maintaining a reaction mixture temperature in the range of 15–20° C. Once the addition was complete the mixture was warmed to 35° C. for 1 hour. At the end of this time a clear and colorless solution was obtained. The reaction mixture was then cooled to room temperature and concentrated under vacuum to a volume of approximately 50 ml. The residue was redissolved in 115 ml of THF and cooled to 0–5° C. using an ice bath. Triethylamine (12 ml, 0.086 mol) was added dropwise to the cooled solution over 30 minutes. The solution was stirred a further 30 minutes after which time the solids were filtered and washed with THF (100 ml). The organics were concentrated under reduced pressure to give the desired compound (4) (14 g, 99%) as a light beige solid. The material was stored under nitrogen at −78° C. in order to avoid decomposition, and used without further purification in subsequent reactions.

All publications and patents identified above are hereby incorporated by reference.

The invention being thus described, it will be obvious that the same may be varied in many ways. Such variations are not to be regarded as a departure from the spirit and scope of the invention and all such modifications are intended to be included within the scope of the following claims.

What is claimed is:

1. A pharmaceutical composition for treating a compulsive disorder, which comprises:
   (i) a compound of formula I

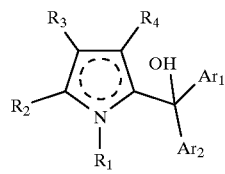

or a pharmaceutically acceptable salt thereof, in an effective amount for treating a compulsive disorder, wherein:
   the compound is an R- or S-enantiomer;
   the ring is saturated or unsaturated;
   $R_1$, $R_2$, $R_3$ and $R_4$ are independently selected from the group consisting of hydrogen, $C_1$–$C_6$ alkyl, hydroxy, carboxy and alkoxy, wherein said $C_1$–$C_6$ alkyl is unsubstituted or substituted, provided that $R_1$, $R_2$, $R_3$ and $R_4$ are not all hydrogen; and
   $Ar_1$ and $Ar_2$ are independently selected from the group consisting of 4-fluorophenyl, 4-chlorophenyl, and 3-methyl-4-fluorophenyl; and
   (ii) a pharmaceutically acceptable carrier, excipient, diluent or combination thereof.

2. The pharmaceutical composition of claim 1, wherein in said compound or pharmaceutically acceptable salt thereof, $R_1$ is selected from the group consisting of methyl, ethyl, propyl and butyl.

3. The pharmaceutical composition of claim 1, wherein in said compound or pharmaceutically acceptable salt thereof, $Ar_1$ is selected from the group consisting of 4-fluorophenyl, 4-chlorophenyl, and 3-methyl-4-fluorophenyl.

4. The pharmaceutical composition of claim 1, wherein in said compound or pharmaceutically acceptable salt thereof, $Ar_2$ is selected from the group consisting of 4-fluorophenyl, 4-chlorophenyl, and 3-methyl-4-fluorophenyl.

5. The pharmaceutical composition of claim 1, wherein said compound is (S)-α,α-Bis(3-methyl-4-fluorophenyl)-2-pyrrolidinemethanol and pharmaceutically acceptable salts thereof.

6. The pharmaceutical composition of claim 1, wherein the compulsive disorder is selected from the group consisting of drug dependence, eating disorders, pathological gambling and Tourette's syndrome.

7. The pharmaceutical composition of claim 6, wherein the compulsive disorder is drug dependence.

8. The pharmaceutical composition of claim 7, wherein the drug dependence is alcohol dependence.

9. The pharmaceutical composition of claim 7, wherein the drug dependence is nicotine dependence.

10. A method for treating a compulsive disorder, which comprises administering to a patient suffering therefrom an effective amount of a compound of formula I

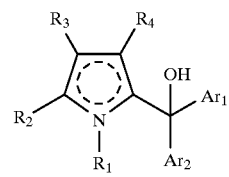

or a pharmaceutically acceptable salt thereof, wherein:
   the compound is an R- or S-enantiomer;
   the ring is saturated or unsaturated;
   $R_1$, $R_2$, $R_3$ and $R_4$ are independently selected from the group consisting of hydrogen, $C_1$–$C_6$ alkyl, hydroxy, carboxy and alkoxy, wherein said $C_1$–$C_6$ alkyl is unsubstituted or substituted; and
   $Ar_1$ and $Ar_2$ are independently selected from the group consisting of an unsubstituted phenyl radical, a monosubstituted phenyl radical, and a multisubstituted phenyl radical, with substituents selected from the group consisting of halogen, $C_1$–$C_6$ alkyl, substituted alkyl, hydroxy, alkoxy, carboxy and mixtures thereof.

11. The method of claim 10, wherein in said compound or pharmaceutically acceptable salt thereof, $R_1$ is selected from the group consisting of hydrogen, methyl, ethyl, propyl and butyl.

12. The method of claim 10, wherein in said compound or pharmaceutically acceptable salt thereof, $Ar_1$ is selected from the group consisting of 4-fluorophenyl, 4-chlorophenyl, and 3-methyl-4-fluorophenyl.

13. The method of claim 10, wherein in said compound or pharmaceutically acceptable salt thereof, $Ar_2$ is selected from the group consisting of 4-fluorophenyl, 4-chlorophenyl, and 3-methyl-4-fluorophenyl.

14. The method of claim 10, wherein said compound is selected from the group consisting of:
   (S)-(−)-α,α-diphenyl-2-pyrrolidinemethanol;
   (R)-(−)-α,α-diphenyl-2-pyrrolidinemethanol;
   (S)-(−)-1-methyl-α,α-diphenyl-2-pyrrolidinemethanol;
   (R)-(+)-1-methyl-α,α-diphenyl-2-pyrrolidinemethanol;
   (S)-(−)-1-ethyl-α,α-diphenyl-2-pyrrolidinemethanol;
   (R)-(+)-1-ethyl-α,α-diphenyl-2-pyrrolidinemethanol;
   (S)-(−)-1-propyl-α,α-diphenyl-2-pyrrolidinemethanol;
   (R)-(+)-1-propyl-α,α-diphenyl-2-pyrrolidinemethanol;

(S)-(−)-1-butyl-α,α-diphenyl-2-pyrrolidinemethanol;
(R)-(+)-1-butyl-α,α-diphenyl-2-pyrrolidinemethanol;
(S)-α,α-Bis(3-methyl-4-fluorophenyl)-2-pyrrolidinemethanol; and
pharmaceutically acceptable salts thereof.

15. The method of claim 10, wherein the compulsive disorder is selected from the group consisting of drug dependence, eating disorders, pathological gambling and Tourette's syndrome.

16. The method of claim 15, wherein the compulsive disorder is drug dependence.

17. The method of claim 16, wherein the drug dependence is alcohol dependence.

18. The method of claim 17, wherein the drug dependence is nicotine dependence.

* * * * *

UNITED STATES PATENT AND TRADEMARK OFFICE
CERTIFICATE OF CORRECTION

PATENT NO. : 5,925,666
DATED : July 20, 1999
INVENTOR(S) : Paul F. Jackson
Barbara S. Slusher It is certified that error appears in the above-identified patent and that said Letters Patent is hereby corrected as shown below:

Column 21, claim 3, line 1, after "claim", replace "1" with "2".

Column 21, claim 4, line 1, after "claim", replace "1" with "2"; and

Column 24, claim 18, line 1, after "claim", replace "17" with "16".

Signed and Sealed this

Eighth Day of February, 2000

Attest:

Q. TODD DICKINSON

*Attesting Officer*  *Commissioner of Patents and Trademarks*